(12) United States Patent
Williams et al.

(10) Patent No.: US 8,085,154 B2
(45) Date of Patent: Dec. 27, 2011

(54) CIRCUIT AND METHOD FOR PROVIDING AN IMPROVED BED PAD MONITOR SYSTEM

(75) Inventors: Steven A. Williams, Hong Kong (CN); Timothy G. Long, Petaluma, CA (US)

(73) Assignee: Smart Caregiver Corporation, Petaluma, CA (US)

( * ) Notice: Subject to any disclaimer, the term of this patent is extended or adjusted under 35 U.S.C. 154(b) by 231 days.

(21) Appl. No.: 12/395,458

(22) Filed: Feb. 27, 2009

(65) Prior Publication Data
US 2009/0212958 A1    Aug. 27, 2009

Related U.S. Application Data

(60) Provisional application No. 61/032,055, filed on Feb. 27, 2008.

(51) Int. Cl.
*G08B 23/00* (2006.01)

(52) U.S. Cl. ...................... 340/573.1; 340/665; 340/667; 5/940

(58) Field of Classification Search ................ 340/573.1, 340/665, 666, 626, 573.7, 667; 5/940; 601/148; 200/85 R
See application file for complete search history.

(56) References Cited

U.S. PATENT DOCUMENTS

| | | | |
|---|---|---|---|
| 6,166,644 A * | 12/2000 | Stroda | 340/573.4 |
| 6,583,727 B2 * | 6/2003 | Nunome | 340/665 |
| 6,847,301 B1 * | 1/2005 | Olson | 340/666 |

* cited by examiner

*Primary Examiner* — Toan N Pham
(74) *Attorney, Agent, or Firm* — Craig M. Stainbrook; Stainbrook & Stainbrook, LLP

(57) ABSTRACT

A circuit and method for providing an improved bed pad, seatbelt or floor mat sensor monitoring system with the ability to detect a connection failure between the monitoring module and the target sensor by monitoring the connection for loss of data being transmitted or returned (looped back) by the sensor.

15 Claims, 11 Drawing Sheets

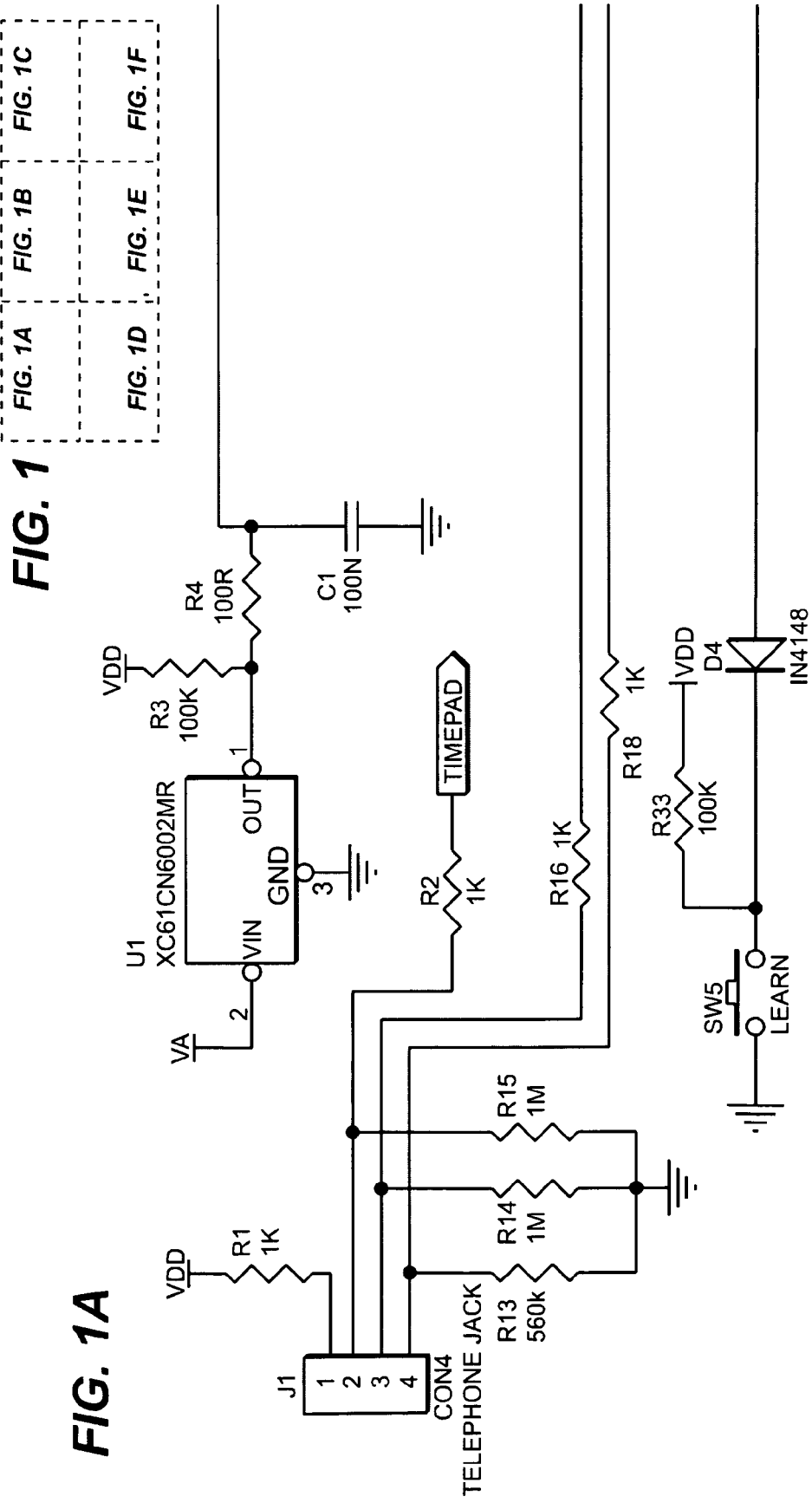

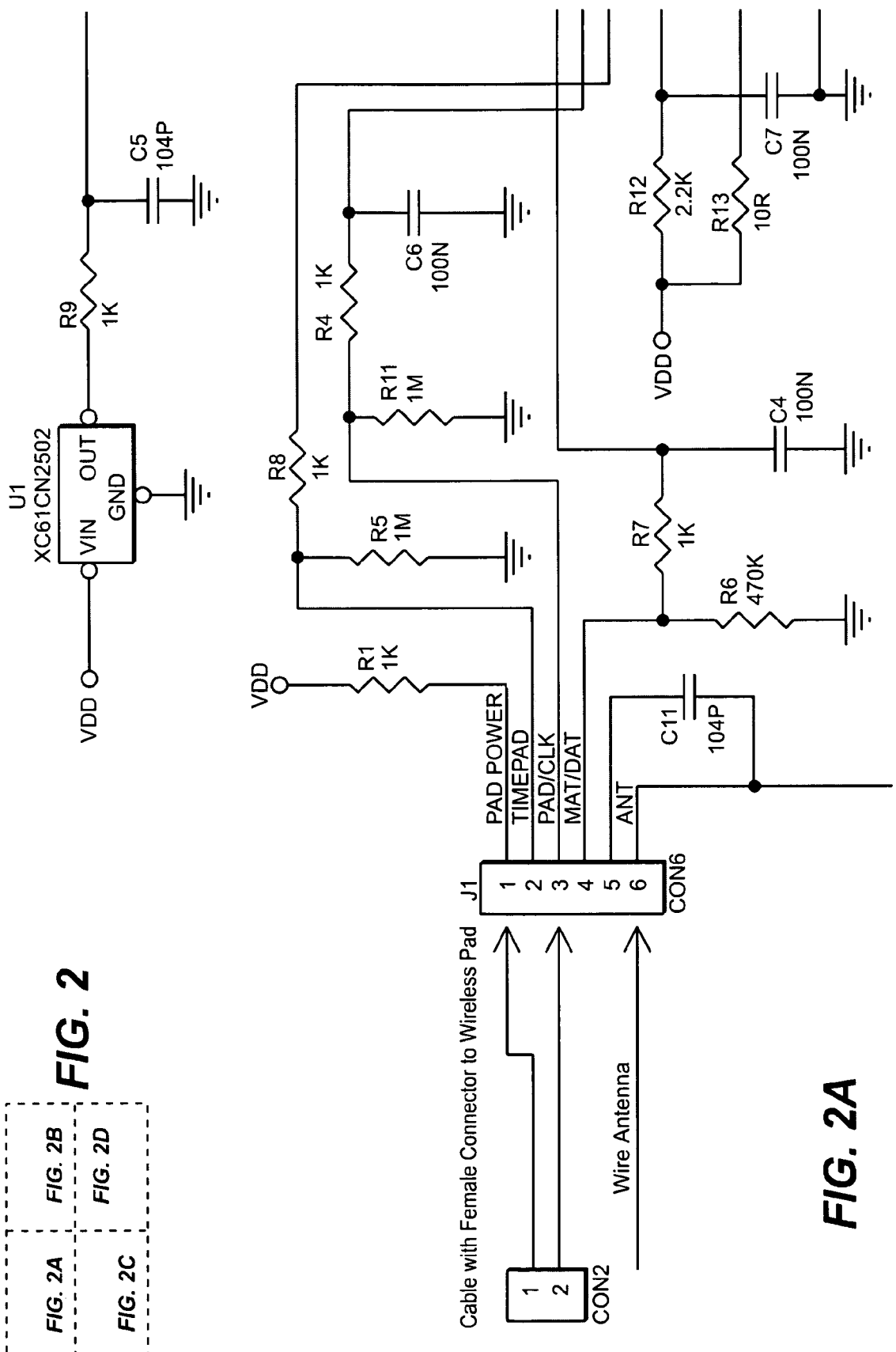

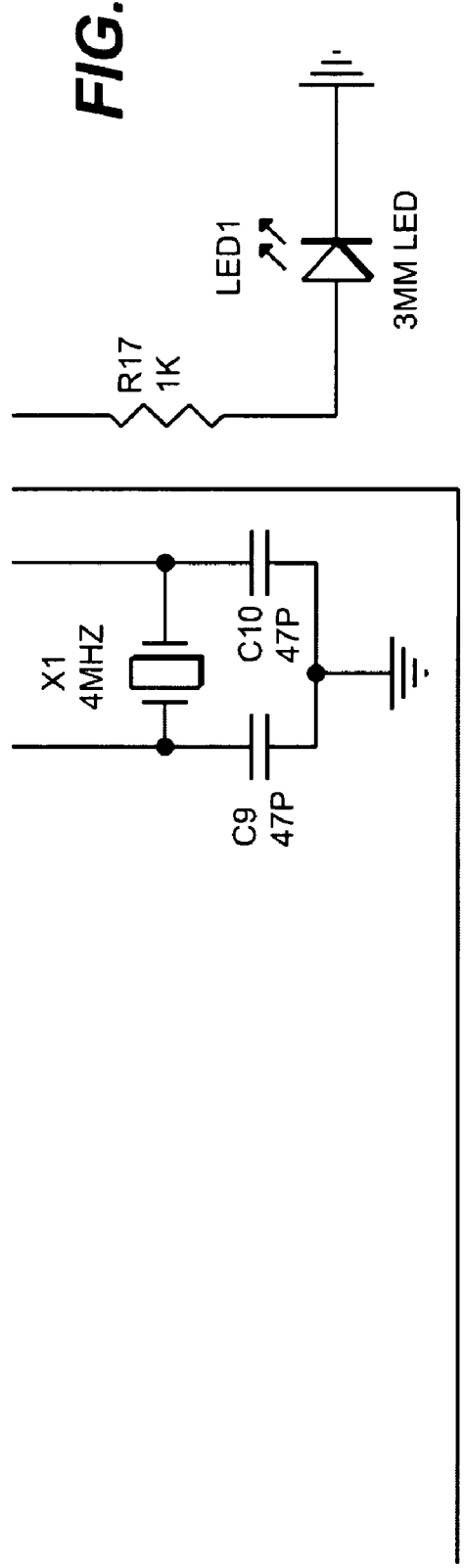

CIRCUIT AND METHOD FOR PROVIDING AN IMPROVED BED PAD MONITOR SYSTEM

CROSS REFERENCES TO RELATED APPLICATIONS

The present application claims the benefit of the filing date of U.S. Provisional Patent Application Ser. No. 61/032,055, filed Feb. 27, 2008 (Feb. 27, 2008).

SEQUENCE LISTING

Not applicable.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

Field of the Invention

The present invention relates generally to portable electronic devices, and, more specifically, to hospital bed patient monitoring systems.

To remotely monitor patients confined to hospital beds, hospitals frequently employ a monitoring system consisting of a "bed pad" sensor. The pad is placed beneath the patient and connected to an electronic monitoring module that issues an alarm signal when it detects that the patient is not on the pad. However, in order to place the monitoring module into monitoring mode, such a system requires that the patient must first be on the bed pad to complete an alarm arming circuit (detected only as an input by prior art monitoring modules). Only after being placed into monitoring mode will the monitoring module detect whether it as been disconnected from the pad and emit an alarm.

A significant shortcoming of the above-described prior art pad-based bed monitor system is that the pad can be disconnected or the alarm cable broken at any time due to movement of the bed while the bed is unoccupied (for instance, by nurses, orderlies, service personnel, or cleaning staff). In the prior art design, unless the bed is occupied when the cable is disconnected or broken, there is no alert sent to staff monitoring the pad indicating to them that the system is inoperable, and therefore patients may be at some risk. The prior art systems do not monitor for this condition before a patient or resident is placed on the pad, and there are documents instances in which patients have been placed on a pad without the caregiver knowing whether the pad is properly attached and functional.

The foregoing discussion of known prior art systems and methods reflect the current state of the art of which the present inventors are aware. Reference to, and discussion of, this knowledge is intended to aid in discharging Applicants' acknowledged duties of candor in disclosing information that may be relevant to the examination of claims to the present invention, when such claims are presented in a non-provisional application claiming the benefit of the filing date of the instant application. However, it is respectfully submitted that none of the above discussed features of prior art discloses, teaches, suggests, shows, or otherwise renders obvious, either singly or when considered in combination, the invention described and claimed herein.

BRIEF SUMMARY OF THE INVENTION

The present invention is a system and method for monitoring proper operation of a bed pad, seatbelt, floor mat sensor and the like. Additionally, this invention detects a loss of connection between the monitoring module and the sensor. While some circuits of the present invention are described in terms of a wired connection between the monitoring module and a bed pad sensor, this should not be construed as limitation of the invention, since this invention also works with wireless monitoring arrangements. Additionally, due to the need for clarity and brevity, the present invention is described in terms of monitoring a hospital bed pad sensor (pad), but this should not be construed as limitation of the invention, since this invention can also function as a monitoring system for a chair pad, seatbelt, floor mat, or other safety device wherein a connection can be made that enables the ability to detect a signal looped through the device, and wherein the signal will fail to loop through the device when the device is not properly configured, connected or functioning.

A key novel feature of the present invention is that the monitoring module interface with the sensor pad is not only used as an input, but also acts as an output for sending data to the pad. To determine whether the monitoring module is properly connected to the pad, the monitoring module regularly sends a signal out to the pad that is returned to the monitoring module through the internal circuitry of the pad. If the signal sent by the monitoring module is not returned, then the monitoring module considers the system to be disabled, and therefore emits an alarm.

In an alternative embodiment of the invention, a data generator module can be incorporated into the sensor pad. In this arrangement, the monitoring module interprets a loss of data signal from the data generator module for more than a predetermined amount of time as a failed connection between the monitoring module and the pad, and therefore emits an alarm when this condition occurs.

The present invention improves dramatically over the prior art in that, if the pad is not properly connected to the monitoring module (or in the case of a wireless connection, the wireless signal connectivity is lost), the monitoring module detects the failure, and emits an alarm to inform the caregiver that the pad is not properly attached to the monitoring module or the pad is not functioning. This alert lets the caregiver know that the system is not fully operational before a patient is placed on the pad.

Accordingly, it will be appreciated that the present invention solves the problems presented by the prior art devices by detecting a correct connection to a bed pad, floor mat, or seatbelt sensor from the moment the monitoring module is first powered up. From that time onward, the connection to the sensor is monitored continuously. The monitoring module accomplishes this by simultaneously using different types of checks. These methods include:

(a) Detection of a DC 'loop' condition through the electrical connections with the sensor. This method only applies where a wired connection exists between the monitoring module and the sensor.

(b) Detection of a returned digital signal through the electrical connections with the sensor. This method applies both in the case where a wired connection exists between the monitoring module and the sensor, as well as in the case where a wireless connection is used.

(c) In an alternative embodiment of the present invention, the system includes detection of a digital signal generated by a data generator module embedded in the sensor (or connected between the monitoring module and the sensor). This method applies both in the case where a wired connection exists between the monitoring module and the sensor, as well as in the case where a wireless connection is used.

It is therefore an object of the present invention to provide a new and improved system for monitoring bed pad sensors, seat belt sensors, floor mat sensors and the like.

A further object or feature of the present invention is a new and improved circuit and method for enabling a monitoring module to evaluate the condition of a connection that is made between the monitoring module and a sensor by way of transmitting a digital signal out through the connection to the sensor and verifying that the same digital signal is received back from a looped circuit inside the sensor.

Another object of this invention is to provide an improved sensor by embedding a data generator module in the sensor. This data generator module is used as a data source whose signal is transmitted through the connection (wired or wireless) to the monitoring module.

An even further object of the present invention is to provide a novel circuit having a wireless signal transmitter under control of a microcontroller that connects to a sensor; the transmitter being modulated with data and keyed on at regular intervals by the microcontroller as long as the physical connection between the microcontroller and the sensor remains properly connected. A monitoring module that includes a wireless receiver remotely receives the regular transmissions made by the transmitter. The loss of these regular "heartbeat" transmissions is interpreted by the monitoring module as a connection failure, thus causing the monitoring module to emit an alarm. This arrangement provides a modular way to adapt prior art sensors to a wireless connection.

Accordingly, an aspect of the present invention is that the monitoring module can be adapted with a modular wireless receiver compatible with the transmitter module contained in the transmitter module circuit.

Other novel features which are characteristic of the invention, as to organization and method of operation, together with further objects and advantages thereof will be better understood from the following description considered in connection with the accompanying drawings, in which a preferred embodiment of the invention is illustrated by way of example. It is to be expressly understood, however, that the drawings are for illustration and description only and are not intended as a definition of the limits of the invention. The various features of novelty that characterize the invention are pointed out with particularity in the claims annexed to and forming part of this disclosure. The invention resides not in any one of these features taken alone, but rather in the particular combination of all of its structures and elements for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE SEVERAL VIEWS OF THE DRAWINGS

The invention will be better understood and objects other than those set forth above will become apparent when consideration is given to the following detailed description thereof. Such description makes reference to the annexed drawings wherein:

FIGS. 1A through 1F comprise a schematic drawing of the monitoring module of the preferred embodiment of the present invention;

FIGS. 2A through 2D comprise a circuit diagram of the transmitter module of the present invention.

DETAILED DESCRIPTION OF THE INVENTION

Referring to FIGS. 1A through 1F, there is shown in schematic form a drawing of the monitoring module of a first preferred embodiment of the present invention. In normal operation, the monitoring module is either physically connected to a bed pad through its legacy monitoring connection, or physically connected to an improved pad that contains an embedded data generator module of the present invention, or connected wirelessly to a transmitter module of the present invention (which is, in turn, connected physically to the pad and continuously monitoring its physical connection with the pad).

Figure 1B:
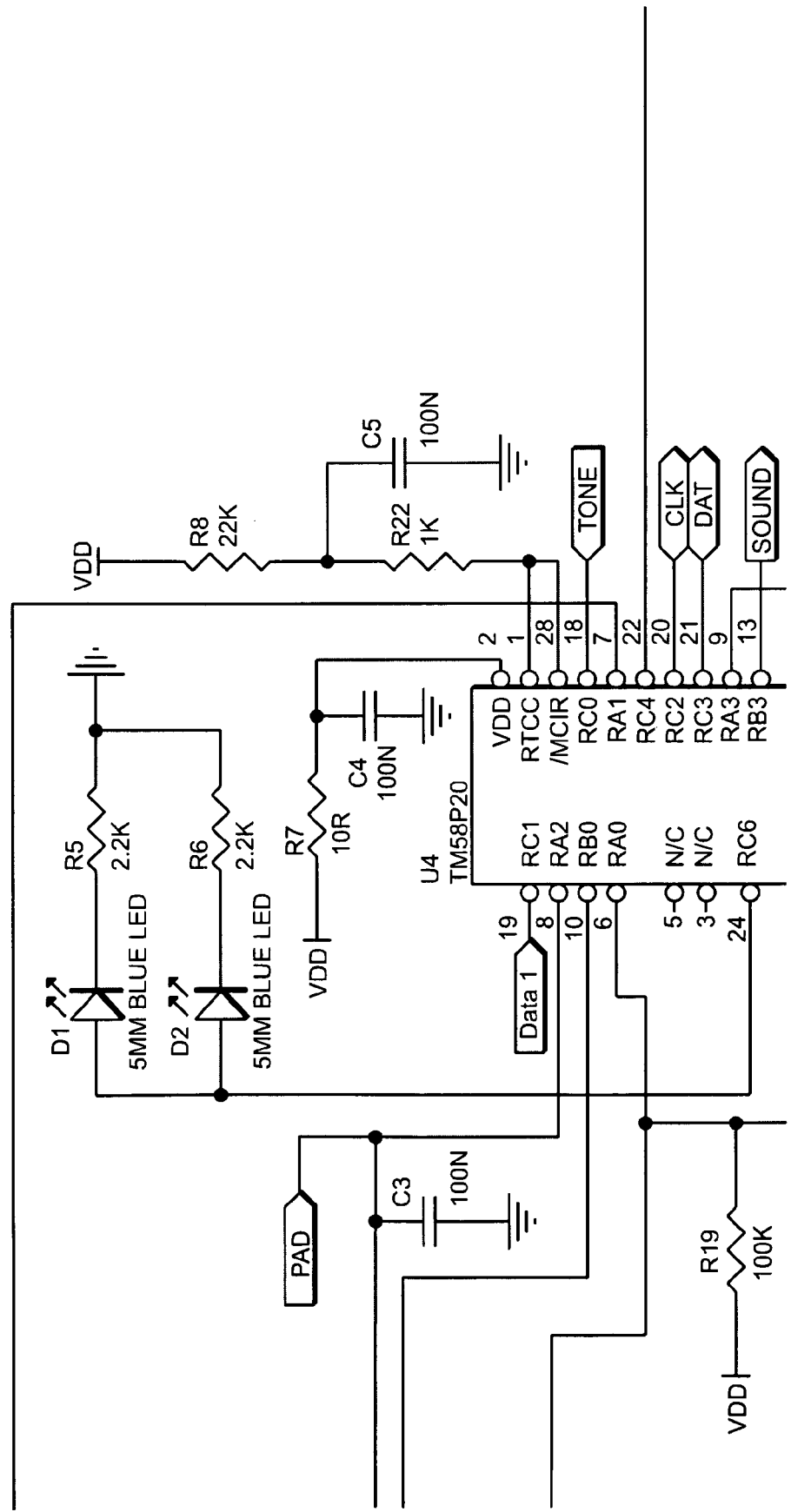
Figure 1C:
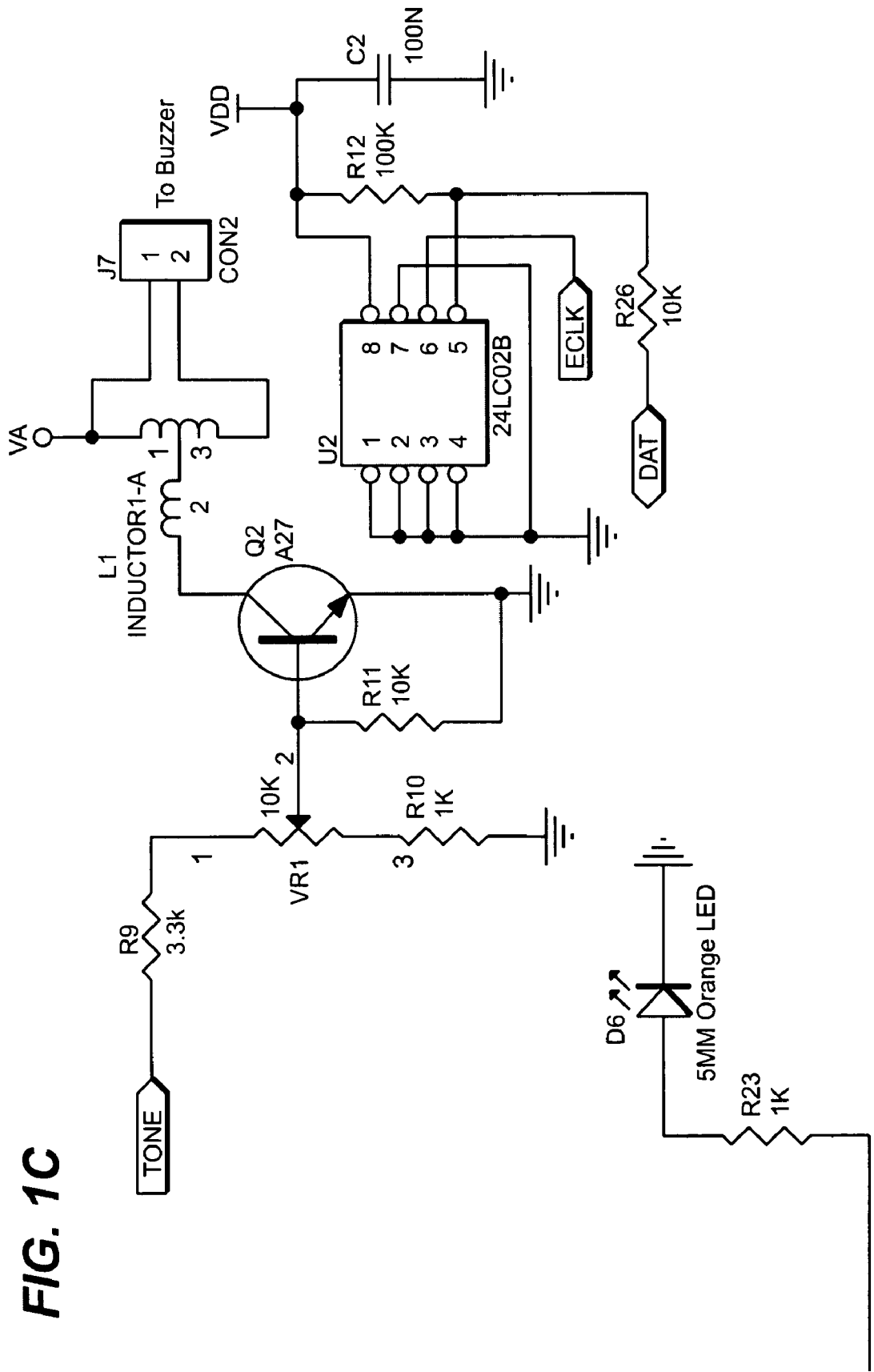
Figure 1D:
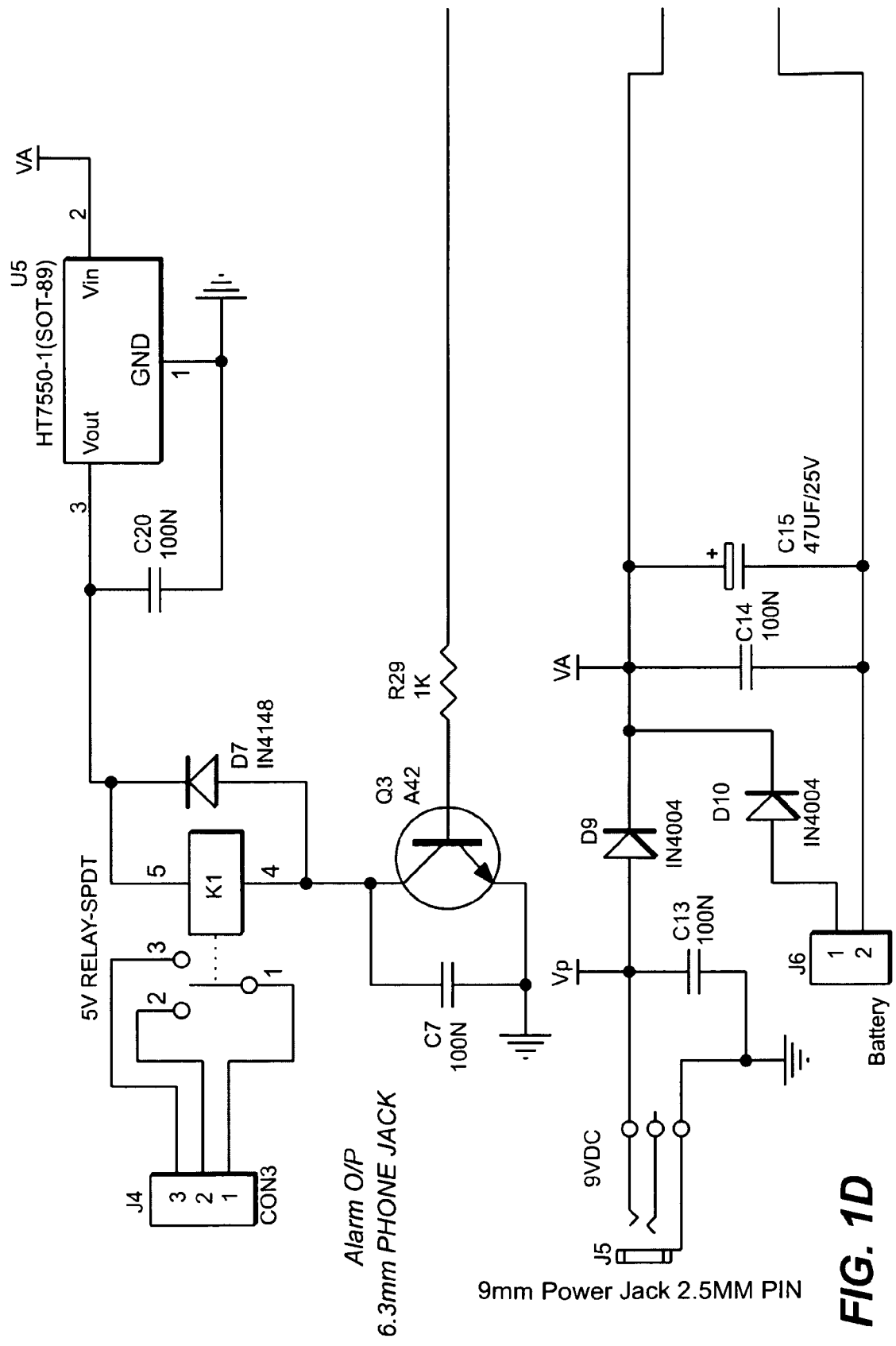
Figure 1E:
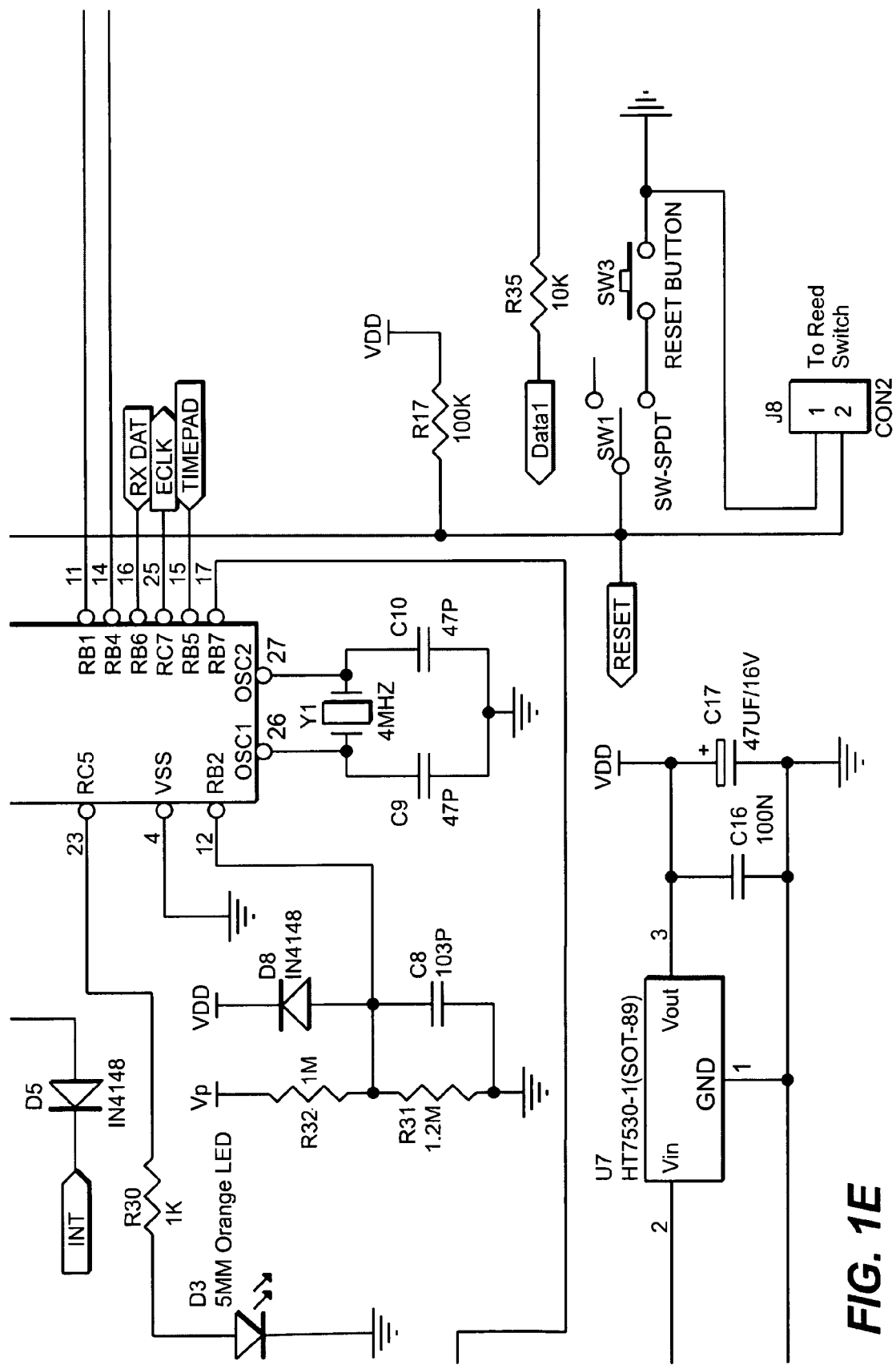
Figure 1F:
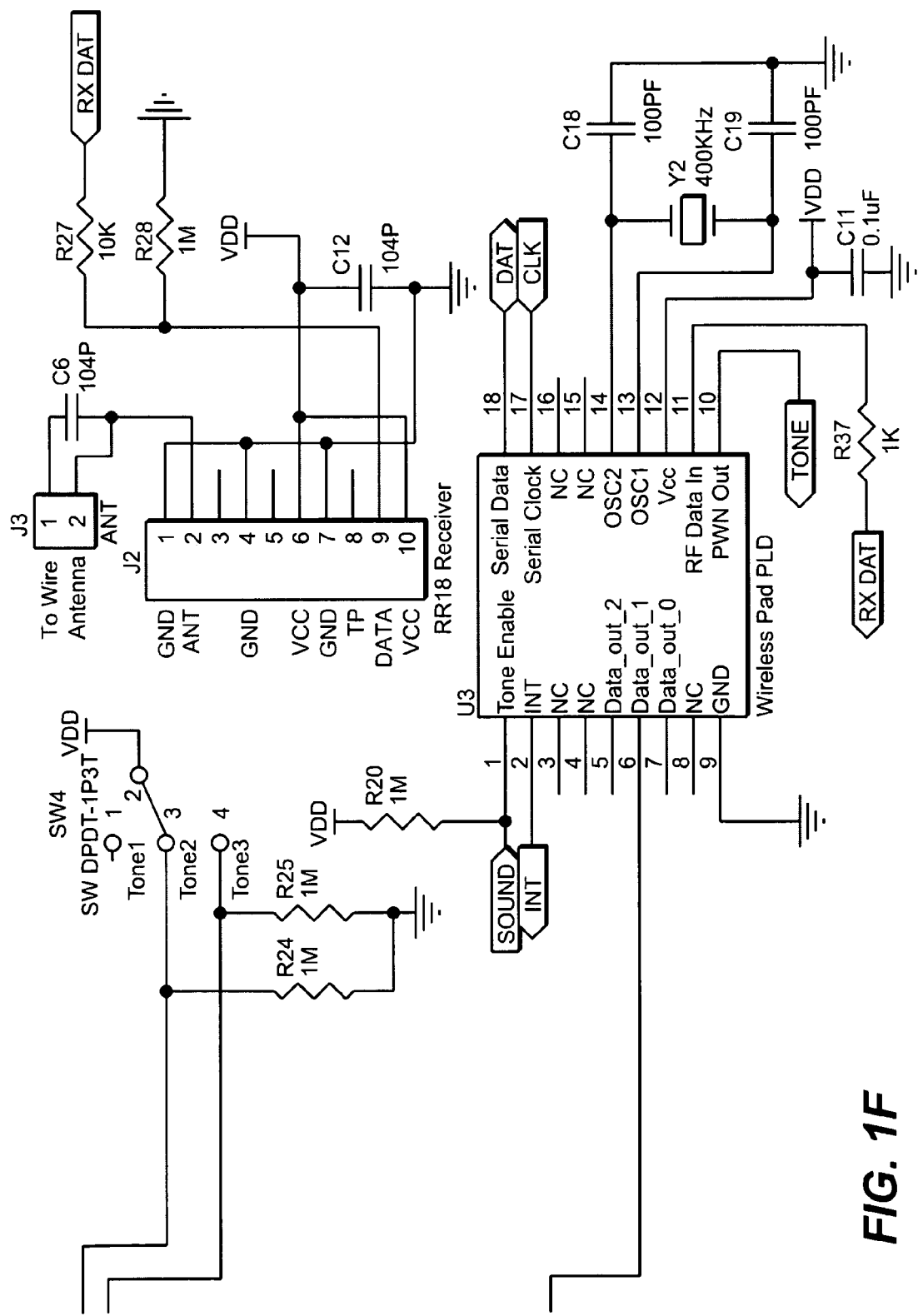

In FIG. 1B it can be seen that microcontroller U4 is the heart of the monitoring module, providing all system control. The software operating on microcontroller U4 dictates the actions of the system based on the inputs to microcontroller U4. The microcontroller input signals include the following:

Pin 7 (RA1) of microcontroller U4 is an input that detects low battery conditions, wherein an the alarm triggers at approximately 7 VDC.

Pin 12 (RB2) of microcontroller U4 is an input that detects loss of AC power through the well-known technique shown in the circuit diagram.

Pin 9 (RA3) of microcontroller U4 is an input that detects the condition of switch SW3 (reset button) to reset the monitoring module after an alarm has been triggered. It should be noted that a magnetic switch connected at connector J8 (CON2) can be used to reset the monitoring module when the manual reset switch has been disabled via switch SW1. The magnetic reed switch can only be closed by a 'caregiver key' since only a caregiver has the magnetic key necessary to reset the monitoring module when switch SW1 is set to disable the manual reset button SW3.

Switch SW4 allows the selection of one of three tone signal types available on the monitoring module (one, two or three-pulse sounds).

The output sounds and indicators provided by the monitoring module are driven by the software operating on microcontroller U4, and include the following:

Relay K1 is available to trigger external 'dry contact' detection alarm systems.

A buzzer or speaker connected at jack J7 sounds when an alarm is triggered. The volume level of the alarm sound is adjustable using variable resistor VR1. The software operating on microprocessor U4 determines the number of alarm sound 'pulses' emitted for each type of alarm condition.

LED D1 ('Check Pad') is illuminated to indicate to a local observer (i.e., a caregiver) that there is a problem with the connection to the pad, or with the pad itself. Pursuant to the program logic of the software operating on microcontroller U4, whenever microcontroller U4 illuminates LED D1, the buzzer or speaker connected to jack J7 also sounds once to alert a local observer (i.e., a caregiver).

LED D2 ('Status/In use') is illuminated to indicate to a local observer (i.e., a caregiver) that the patient is on the pad and that the system is working correctly.

LED D3 ('Alarm led/low battery') is illuminated to indicate to a local observer (i.e., a caregiver) that an alarm is active or that the battery needs to be changed. Note that LED D3 illuminates in this condition even if the monitoring module sound is turned off.

Power is provided to the circuits of the monitoring module through the power regulation and filtering section comprised of capacitors C13, C14, C15, C16 and C17, diodes D9 and D10 and voltage regulator U7. The output of voltage regulator U7 is a regulated and filtered 9 VDC constant voltage source.

A battery pack connected to jack J6 provides emergency backup power when AC power fails or is disconnected. A commercial AC-to-9 VDC 'wall wart' power adaptor is connected to DC power input connection jack J5 to provide power to the monitoring module from the commercial AC power source.

Jack J1 (CON4) provides a wired connection between the monitored bed pad and the monitoring module circuit. Unlike most units this connection is not a simple DC loop testing input connected to the pressure pad, but has the following additional features:

The wired connection of jack J1 includes two input-only pins (pin 3 and 4), one output pin (pin 2) and one VDD source (pin 1).

Pin 3 of jack J1 is connected through resistor R16 to pin 8 (RA2) of microcontroller U4. Microcontroller U4 thus monitors the conditions present on Pin 3 of jack J1. Pin 3 of jack J1 is also connected (via the wired connection to the pad) to one side of the pad's internal alarm loop circuit, which, in prior art pads is always short-circuited (or a non-open circuit) to pin 2 of the pad's connector when the pad is properly connected to the monitoring module. Pin 2 of jack J1 is connected via isolation resistor R2 to pin 15 (RB5) of microcontroller U4. Microcontroller U4 can either transmit a digital signal to the pad on Pin 2 of Jack J1, or generate a DC voltage on the pin.

In the event a digital signal is imposed onto pin 2 of jack J1, microcontroller U4 is set to expect and detect the same signal looped to itself via the internal circuit of the pad and back through pin 3 of Jack J1. If the signal is not seen looped back, microcontroller U4 of the monitoring module causes an alarm to be emitted.

When an analog DC voltage is imposed onto pin 2 of jack J1, microcontroller U4 is set to expect and detect a voltage looped to itself via the pad internal circuit and back through pin 3 of Jack J1. If the original voltage (or some predetermined residual amount of that voltage) is not seen looped back, microcontroller U4 of the monitoring module causes an alarm to be emitted.

Another solution is simply detecting on pin 2 of Jack J1 the looped bad VCC signal from Pin 1. This is looped back by a connection on the pad and is not present if the pad is removed.

When the monitoring module is connected to an improved pad having the embedded data generator module of this invention (illustrated in FIG. 3), pin 4 of jack J1 on the monitoring module receives the data signal sent through the connections between the pad and the monitoring module by the embedded data generator module. Pin 4 of jack J1 is connected through resistor R18 to pin 10 (RB0) of microcontroller U4. Microcontroller U4 is set to expect and detect the digital signal continuously through this path. If the signal is not seen for some predetermined amount of time, microcontroller U4 of the monitoring module causes an alarm to be emitted. The circuit actually shows a memory chip (but other chips such as processors can be used). In this case Pin 1=VCC, Pin 2=0V, pin 3=Clock to synchronize data, Pin 4=Data (in and out). The bed monitor processor sends data to the memory chip and then reads back to make sure it is still in the circuit. It also updates the chip for the countdown timing function in the CPI bed monitor.

When the monitoring module is monitoring the pad via the wireless transmitter module (shown in FIGS. 2A through 2D) that is physically connected to the pad, the monitoring module expects to receive a wireless transmission regularly from the wireless transmitter module. If the wireless signal (modulated with data containing the correct digital address) is not detected within a predetermined amount of time, the monitoring module issues a 'check pad' alarm.

In this arrangement, the monitoring module has a receiver module connected to jack J2. The baseband signal of the receiver is passed to programmable logic device U3, which acts as a decoder chip that retrieves the digital information from the received wireless signal and sends the results to microcontroller U4 for interpretation. Microcontroller U4 is configured to stay in low current consumption mode until an interrupt is received from programmable logic device U3 to reduce power consumption. At least one component of the digital content of the wireless signal is the digital address of the wireless transmitting module. In this manner, the wireless transmission received can be verified as coming from the transmitter module of interest.

In order to avoid transmitted signal collisions when more than one system is used in close proximity (within wireless signal range of each other), the time between transmissions is different for each transmitter module, depending on the unique digital address programmed into the memory of each transmitter module.

Regardless of which of the possible operating configurations are chosen, the checks for proper connection between the pad and the monitoring module are made continuously from the time the monitoring module is powered up, so a caregiver can know the status of the monitoring system as a whole before a patient is even placed on a bed pad.

Referring next to FIGS. 2A through 2D, there is shown a circuit diagram of the transmitter module used in the present invention. The transmitter module is controlled by software operating on microcontroller U2. As an alternative, a transceiver may be used on both the bed monitor and pad wireless pad unit. This would allow for two way communication and frequency channel hopping to overcome interference problems.

In normal operation the transmitter module is physically connected (via jack CON2 and jack J1 (CON6)) to the bed pad being monitored. Microcontroller U2 of the transmitter module continuously checks the integrity of the physical connection between the bed pad and the transmitter module. As long as physical connection between the bed pad and the transmitter module is proper, microcontroller U2 regularly causes the transmitter module connected to jack J3 to emit wireless signals modulated with data that include the unique digital address of the transmitter module. In this condition, microcontroller U2 also regularly illuminates LED 1 to indicate that the connection is good. If the physical connection between the bed pad and the transmitter module is broken or fails, microcontroller U2 stops causing the transmitter to emit wireless signals, and also stops illuminating LED 1, thus indicating the failure.

Figure 2B:
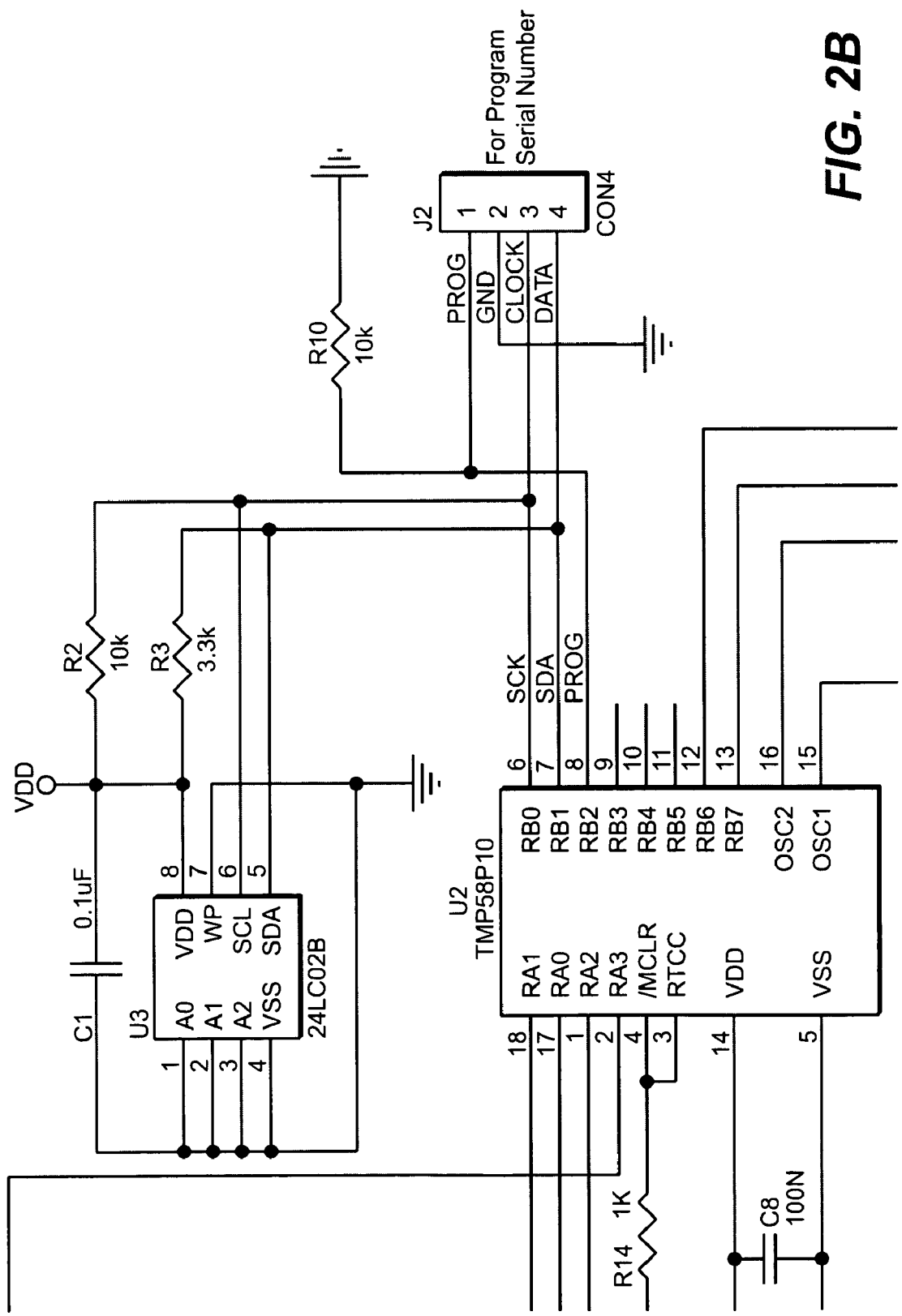

Still referring to FIG. 2B, it can be seen that microcontroller U2 is able to detect the conditions of the connection between the transmitter module and the pad in a manner similar to that used by the monitoring module. Pin 2 of jack J1 is used by microcontroller U2 to send a digital signal to the pad, which is looped back via the pad's internal circuit to pin 3 of jack J1. Pin 3 of jack J1 is connected via isolation resistor R4 to pin 17 (RA0) of microcontroller U2, so that microcontroller U2 can monitor whether the digital signal sent out on pin 2 of jack J1 arrives back intact at pin 3 of jack J1. If the digital signal is not seen at pin 3 of jack J1 for more than a predetermined amount of time, the condition is interpreted by microcontroller U2 as a failure of the connection or the pad itself.

Figure 2C:
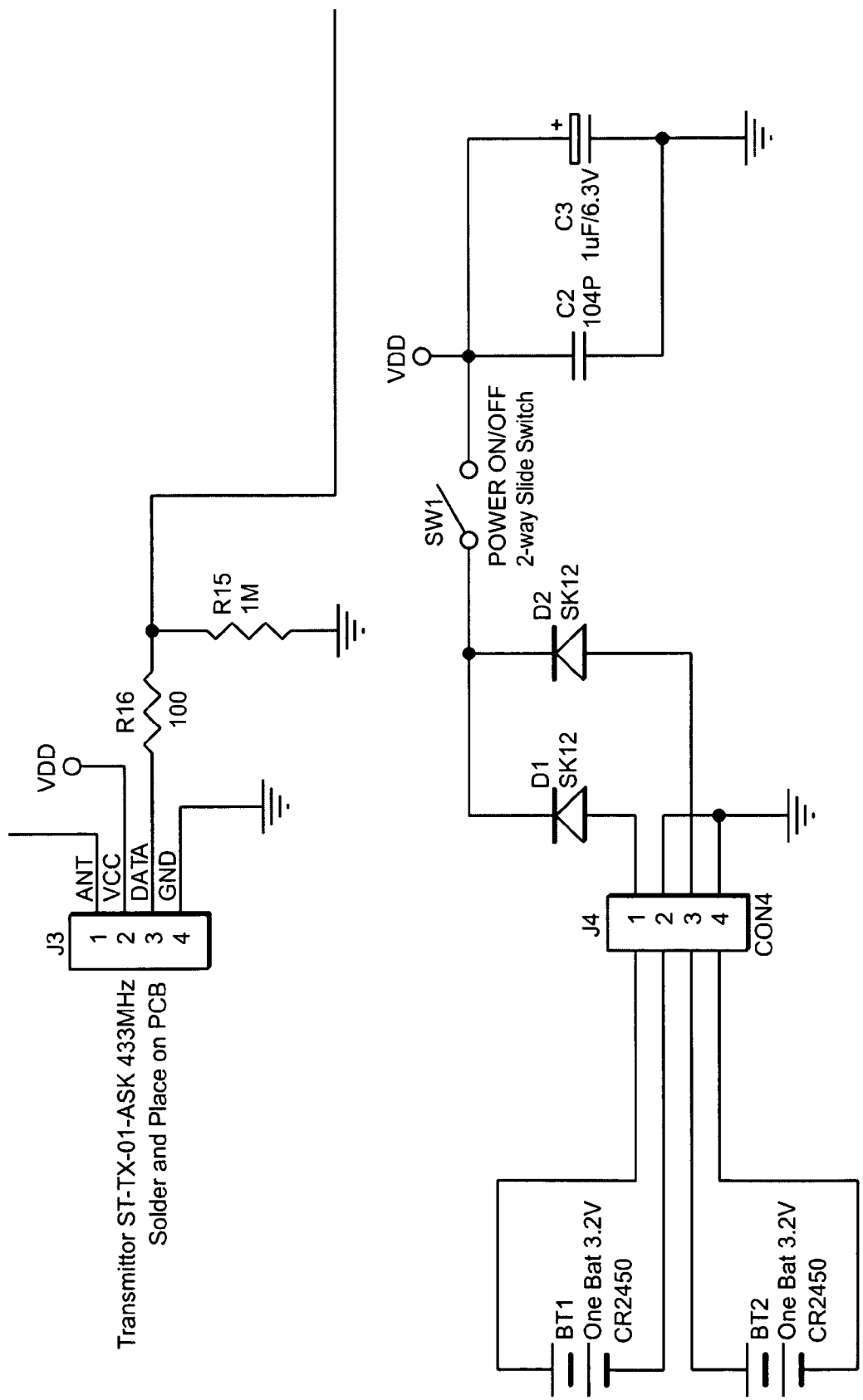

Still referring to FIG. 2C, it can also be seen that power is provided to the transmitter module by two lithium button cell batteries through their connection with jack J4. These cells have sufficient power storage to last between two and three years under normal operating conditions.

Figure 3:
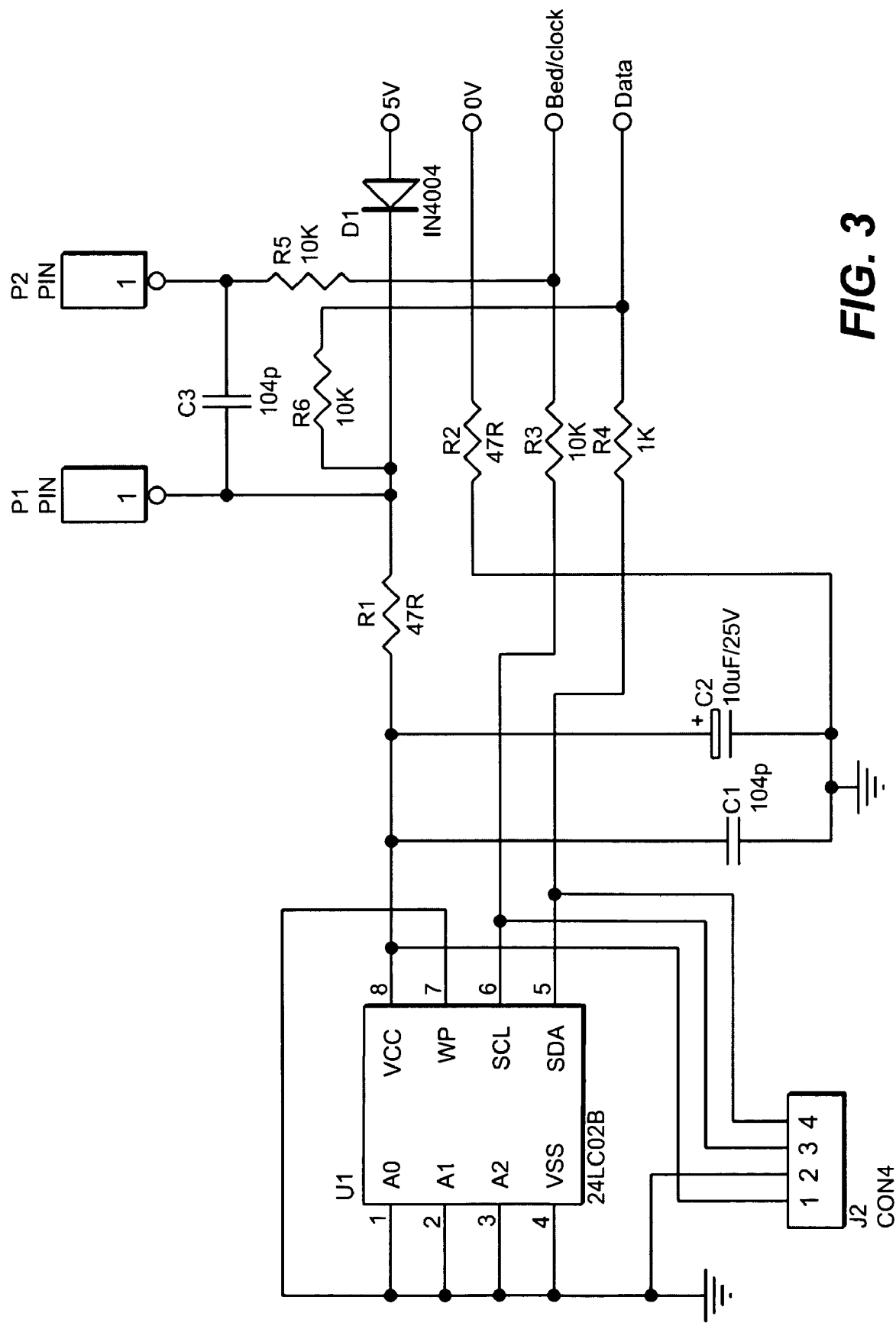
FIG. 3 is a circuit diagram of a data generator module that can be incorporated into a bed pad sensor.

Referring now to FIG. 3, there is shown a schematic circuit diagram of a data generator module that can be incorporated into a bed pad sensor. In normal operation, this module is connected to jack J1 of the monitoring module via a wired connection. In this configuration, any digital signals generated by the monitoring module that are received on pin 2 of jack J2 (CON4) of the data generator module are shunted to ground. Pin 1 of jack J2 (CON4) of the data generator module is used to receive the power source (VCC) for chip U1 of the module. Chip U1 of the data generator module, when powered up by the presence of VCC, continuously generates a repeating data pattern at pin 4 of jack J2 (CON4), as well as continuously generating a clock signal at pin 3 of jack J2. In order to verify that the connection between the monitoring module and the pad is good, the monitoring module can continuously monitor these signals due to the pin-for-pin connection between jack J2 (CON4) of the data generator module and jack J1 of the monitoring module.

Although the above is a possible solution in this diagram, the EEPROM memory chip has data programmed into it and this is addressed serially by the clock (3) and data (4) pins. This can be to read out data from the memory chip or to program/update data on the memory chip. This is how the count down is done on the CPI monitor; that is, the monitor reads in the number decreases by one and programs it back into the chip. However, it also means that if the monitor is not able to read the chip, then there is a fault and the pad has likely been removed.

In the ways described above, the present invention provides a sensor connection integrity monitoring system that is significantly improved over the prior art, offering a substantial benefit to the user by preventing undetected system failures.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

What is claimed as invention is:

1. A system for monitoring patient pressure pad operation, comprising:
    a monitoring module for continuously checking for a proper connection with a sensor in a pressure pad from the time said monitoring module is powered up;
    a pressure pad including a sensor in electrical communication with said monitoring module;
    signal detection means in said monitoring module for detecting a proper connection, or a lack thereof, between said monitoring module and said sensor; and
    an alarm for producing a perceivable output connected to said signal detection means;
    wherein said monitoring module continuously sends a signal to said pressure pad, and wherein if said signal sent by said monitoring module is not returned for any reason, said monitoring module considers said pressure pad to be disabled and initiates an alarm.

2. The system of claim 1, wherein said monitoring module and said sensor are connected through a wired connection.

3. The system of claim 1, wherein said monitoring module and said sensor are in electrical communication through a wireless connection.

4. The system of claim 1, wherein said pressure pad is selected from the group consisting of bed pad, chair pad, seatbelt, and floor mat.

5. The system of claim 1, wherein said signal detection means includes means to detect a signal looped through said system and will fail to detect a signal looped through said system when said system is not properly configured, connected or functioning.

6. The system of claim 1, wherein said signal detection means determines whether said monitoring module is properly connected to said sensor by regularly sending a signal to said sensor and the signal is returned to said monitoring module through a circuit internal to said pressure pad.

7. The system of claim 1, wherein said pressure pad further includes a data generator module for providing an output data signal, and wherein said monitoring module includes means for detecting a loss of data signal from said data generator module.

8. The system of claim 7, wherein when said monitoring module detects a loss of the output data signal for more than a predetermined amount of time, said monitoring module interprets this loss as a failed connection between said monitoring module and said sensor and sends an output signal to said alarm.

9. The system of claim 1, wherein said monitoring module and said sensor are connected through a wired connection and said signal detection means detects a DC loop condition through said wired connection.

10. The system of claim 1, wherein said signal detection means detects a returned digital signal through the electrical connection between said monitoring module and said sensor.

11. The system of claim 10, wherein said connection between said monitoring module and said sensor is a wired connection.

12. The system of claim 10, wherein said connection between said monitoring module and said sensor is a wireless connection.

13. The system of claim 1, further including a data generator module, and wherein said signal detection means detects a digital signal generated by said data generator module.

14. The system of claim 13, wherein said data generator module is incorporated in said sensor.

15. The system of claim 13, wherein said data generator module is incorporated in a connection between said monitoring module and said sensor.

* * * * *